United States Patent
McGlothlin et al.

[11] Patent Number: 5,992,700
[45] Date of Patent: Nov. 30, 1999

[54] CONTROLLED GAS GENERATION FOR GAS-DRIVEN INFUSION DEVICES

[75] Inventors: Mark W. McGlothlin; Alice A. DePaul; Eric Schmid, all of San Diego, Calif.

[73] Assignee: Apex Medical Technologies, Inc., San Diego, Calif.

[21] Appl. No.: 08/864,630

[22] Filed: May 28, 1997

[51] Int. Cl.$^6$ .................................................. B67D 3/00
[52] U.S. Cl. ...................... 222/187; 222/386.5; 222/394; 222/396
[58] Field of Search ............................. 222/95, 105, 187, 222/386.5, 394, 396, 399

[56] References Cited

U.S. PATENT DOCUMENTS

| | | | |
|---|---|---|---|
| 4,646,946 | 3/1987 | Reyner | 222/386.5 |
| 5,009,340 | 4/1991 | Morane | 222/386.5 |
| 5,035,351 | 7/1991 | Moran | 222/386.5 |
| 5,169,390 | 12/1992 | Athayde et al. | 604/141 |
| 5,234,140 | 8/1993 | Demarest et al. | 222/399 |
| 5,398,850 | 3/1995 | Sancoff et al. | 222/386.5 |
| 5,398,851 | 3/1995 | Sancoff et al. | 222/386.5 |
| 5,516,004 | 5/1996 | Lane | 222/386.5 |
| 5,553,741 | 9/1996 | Sancoff et al. | 222/386.5 |
| 5,558,255 | 9/1996 | Sancoff et al. | 222/189.06 |
| 5,578,005 | 11/1996 | Sancoff et al. | 604/82 |
| 5,588,556 | 12/1996 | Sancoff | 222/1 |
| 5,700,245 | 12/1997 | Sancoff et al. | 604/145 |

FOREIGN PATENT DOCUMENTS

WO 94/05354  3/1994  WIPO.
WO 97/02849  1/1997  WIPO.

*Primary Examiner*—Joseph A. Kaufman
*Attorney, Agent, or Firm*—Townsend and Townsend and Crew LLP

[57] ABSTRACT

Gas is generated at a controlled rate from a liquid and solid phase combination that generated gas upon contact, by using diffusive transport of the liquid toward the solid phase surface to prolong the rate of gas generation, with a variety of alternatives for controlling the rate of diffusive transport. This system is useful in infusion devices for delivering medications or other beneficial liquids from a retaining pouch at controlled rates over a prolonged period of time.

32 Claims, 4 Drawing Sheets

CONTROLLED GAS GENERATION FOR GAS-DRIVEN INFUSION DEVICES

BACKGROUND OF THE INVENTION

1. Field of the Invention

This invention resides in the field of controlled liquid delivery devices, such as those used in the administration of medicaments. This invention also relates to the chemistry of gas generation used as the driving force in controlled liquid delivery devices, and the types of materials used as sources of the gas.

2. Description of the Prior Art

Infusion pumps are devices that eject liquid materials at continuous and prolonged rates by generating gas in a contained enclosure that forces the liquid material out of a bladder or reservoir retained within the enclosure. Pumps of this type are useful for the controlled delivery of drugs and other medications to patients, eliminating the need for periodic injections or other modes of administration, and avoiding the usual profile of a high initial concentration of the drug in the bloodstream followed by a gradual decline.

Numerous patents have issued on inventions relating to infusion pump design. Representative examples are U.S. Pat. Nos. 3,023,750 (Baron, Mar. 6, 1962), 4,379,453 (Baron, Apr. 12, 1983), 3,718,236 (Reyner et al., Feb. 27, 1973), 5,398,850 (Sancoff et al., River Medical, Inc., Mar. 21, 1995), 5,398,851 (Sancoff et al., River Medical, Inc., Mar. 21, 1995), 5,588,556 (Sancoff et al., River Medical, Inc., Dec. 31, 1996), 5,578,005 (Sancoff et al., River Medical, Inc., Nov. 26, 1996), 5,558,255 (Sancoff et al., River Medical, Inc., Sep. 24, 1996), and 5,106,374 (Apperson et al., Abbott Laboratories, Apr. 21, 1992), all of which disclose various devices that generate pressurized gas to expel a liquid from a liquid delivery device, utilizing chemically reactive sets or combinations of gas-generating chemicals.

The Baron and Reyner et al. patents disclose liquid delivery systems powered by the generation of carbon dioxide gas by reactive chemical combinations, but they lack means to control the reaction rate or the resulting liquid flow. The Reyner et al. patent discloses a system that produces a series of sequential chemical reactions that release gas in a series of discrete releases over a period of time.

The systems disclosed in the Sancoff et al. patents achieve controlled delivery primarily by extending the reaction time of the reactants. This is achieved by adding a rate-limiting moiety to a solid tablet consisting of an alkaline metal carbonate, and then submerging the tablet in a bath of aqueous acid media. The Sancoff et al. patents specify separate storage of the chemical reactants prior to use, with no premixing. The reaction rate upon initial contact of the chemicals is very high, and drops off rapidly with time as the reactants are consumed. The rate of reaction is a function of the concentration of remaining chemicals, and as the liquid acid reactant concentration decreases significantly over time, the reaction rate and hence the rate of carbon dioxide generation are reduced. While the exposed surface area of solid reactant increases with time, this does not fully compensate for the decreased liquid reactant concentration. Accordingly, a very large portion of the generated gas is wastefully vented through a pressure relief valve during the early part of the infusion process.

The Sancoff et al. patents disclose the use of two separately disposed chemical reactants, one liquid and one solid. Both reactants are dangerous to handle, and can pose a health risk to patients and health care workers in the event of a leak. To initiate the reaction in the device, a barrier membrane is ruptured and the solid alkaline tablet is manually pushed into the acid solution. This is accomplished by pressing against a portion of the exterior wall of the device, the wall portion being of reduced thickness. Unfortunately, this reduced thickness portion is a prone to leakage. Also, the pressing of the tablet through the barrier membrane must be done rapidly. Otherwise, back pressure from the resulting gas can arrest the movement of the tablet through the membrane when the tablet is only part way through. A tablet resting part of the way through the membrane can cause failure of the device.

The Apperson et al. patent discloses an infusion device which releases compressed gas from a storage cylinder at a controlled rate to power an infusion device. Gas pressure in this device is maintained by use of a pressure relief valve. In order to store the required amount of gas to power the device, it is necessary to store either a large volume of gas under low pressure or a small volume under high pressure. Neither is desirable since low pressure storage is subject to space limitations and high pressure gas entails excess weight and cost, as well as the risk of damage and injury. High pressure gas also requires a relatively high pressure gas regulator or relief valve, both of which are expensive.

Further disclosures of potential relevance to the present invention include U.S. Pat. Nos. 3,888,998 (Sampson et al., The Procter & Gamble Company, Jun. 10, 1975), 3,992,493 (Whyte et al., The Procter & Gamble Company, Nov. 16, 1976), 4,007,134 (Liepa et al., The Procter & Gamble Company, Feb. 8, 1977), and 4,025,655 (Whyte et al., The Procter & Gamble Company, May 24, 1977). These patents disclose the use of carbon dioxide loaded (adsorbed) onto molecular sieve materials, with subsequent desorption for the purpose of carbonating water for use in carbonated beverages. These systems are designed to rapidly desorb carbon dioxide into water over a period of about one to five minutes only, and for the sole purpose of carbonating water. The molecular sieves can be formed into various shapes and loaded with adsorbed carbon dioxide, then immersed into water, a portion of which is adsorbed in preference to the previously adsorbed carbon dioxide, producing carbon dioxide gas bubbles which carbonate the water for use in beverages. The entire gas release process generally takes place in less than about five minutes, and no attempt is made to capture work from the released gas.

SUMMARY OF THE INVENTION

It has now been discovered that gas can be generated by desorption, chemical reaction, or other means resulting from the contact between liquid and solid phases in a prolonged and controlled manner by diffusing the liquid to the surface of the solid at a controlled difflusion rate. Various means of limiting and controlling the diffusion rate are disclosed, including the use of wicks and wicking methods, as well as the use of additives mixed in with the liquid to lower its concentration or to vary certain properties of the liquid that affect its difflusion rate. Included among the structures disclosed are those in which the liquid and solid substances are physically separated by barriers, with a wick serving as the sole means of communication, as well as those in which the solid substance is porous with the liquid occupying the pores but permitted only limited diffusion within the pores by the additives, examples of which are diluents and viscosity-increasing solutes. Gas generation in each of the various configurations of the invention is provided by any of a variety of mechanisms, including gas-generating chemical reactions and the release of adsorbed gases.

This discovery is applicable to any device that can benefit from a controlled release of gas. Prominent among such devices are infusion pumps, in which the released gas provides the driving force for the pressurized expulsion of liquid medicament or other beneficial liquid to an environment where the liquid has a beneficial effect. In these devices, the beneficial liquid is held in a bladder that contains at least one (preferably only one) opening, the bladder retained in a housing of material that is gas-impermeable or very low in gas permeability. The housing material is also substantially non-extensible, i.e., extensible by no more than about 5%, and preferably by no more than about 1%, along a linear dimension upon exposure to the pressures typically encountered during use according to this invention. In addition, the housing material is preferably flexible. The housing further contains the solid and liquid substances that generate the driving gas upon contact.

A further discovery made in connection with this invention is the choice of a laminate as the wall material for the housing and the effectiveness of the laminate in providing optimal flexibility while still serving as an effective barrier to gas permeation. A still further discovery is a novel design for a pressure relief valve, including structure within the valve to permit adjustment of the relief pressure and materials used in the valve to prevent blocking of the valve.

Still further discoveries in connection with this invention are chemical systems that are particularly adaptable for generating gas in a controlled manner for infusion devices, and that avoid the risks of hazardous discharge or air/gas separation devices, which are expensive and subject to blockages and clogging. One such system is a molecular sieve material bearing an adsorbed gas as the solid phase, in combination with an aqueous liquid as the liquid phase. As the water in the aqueous liquid contacts the molecular sieve at a controlled and prolonged rate, the adsorbed gas is released. Another such system is a liquid solution of hydrogen peroxide or a superoxide compound as the liquid phase and an immobilized catalyst or enzyme as the solid phase, the catalyst or enzyme promoting the decomposition of the peroxide or superoxide to release oxygen gas. A controlled rate of contact and hence a controlled release of gas in either system is enhanced by the use of the controlled diffusion methods described above.

These and other discoveries, features and embodiments of the invention will be understood in more detail from the descriptions that follow.

DETAILED DESCRIPTION OF THE INVENTION AND PREFERRED EMBODIMENTS

The present invention is susceptible to a wide range of implementations and embodiments, and certain aspects of the invention as a whole will be best understood by the detailed explanation of specific examples. This portion of the specification will begin by examining the chemical aspects of the invention, and will then proceed with explanations of the structural features by specific examples.

Wicking Materials and Methods

In certain embodiments of this invention, as indicated above, controlled diffusive transport of the liquid phase to the solid phase is achieved by the use of a wick joining the liquid reservoir to the solid phase. The rate of gas desorption or generation from the tablet is roughly proportional to the rate of liquid flow through the wick into the solid phase. The rate of flow through the wick can be varied by a number of techniques, including varying the cross sectional area of the wick, varying the amount of the wick immersed in the liquid reservoir, or by selection of the wicking material, such as a crosslinked polyvinyl alcohol for highly efficient transport. The rate of flow through the wick can be lowered by decreasing the cross sectional area of the wick, increasing the viscosity of the liquid, shortening the wick, pinching or crimping the wick, or adding a restriction to the wick.

A wide variety of wick materials can be used; the particular material is not critical to the invention. Examples of wick materials are polyvinyl alcohol (preferably crosslinked), polyvinyl acetate (preferably crosslinked), combinations of polyvinyl alcohol and polyvinyl acetate (preferably both crosslinked), crosslinked hydrogels, felts, open-cell sponge materials, and porous plastics. Preferred wick materials for certain embodiments of the invention are polyvinyl alcohol or combinations of polyvinyl alcohol and polyvinyl acetate. These materials are available commercially from Merocel Corporation (Mystic, Conn. USA), Kanebo Ltd. (Osaka, Japan), and other suppliers. A most preferred wicking material is Kanebo Type E(A), with an average pore size of 130 microns and apparent density of about 0.11 g/cm$^3$. A description of one type of wick useful in this invention is found in U.S. Pat. No. 4,098,728 (Rosenblatt, Jul. 4, 1978, incorporated herein by reference), and available from Merocel Corporation. The Rosenblatt wick is naturally hydrophilic, and can be made dense enough to prevent a rapid flow of water into the molecular sieve tablet, even with significant head pressures applied. The Rosenblatt wick material can be obtained in flat sheets and die cut to the desired final dimensions. A currently preferred wick cross section is 2 mm×2 mm.

To achieve a very slow gas evolution rate, a slow wicking material can be used. For systems using water as the liquid phase, crosslinked hydrogels serve as slow wicking materials. One example is a cross-linked hydrogel containing about 4% very high molecular weight polyethylene oxide and about 96% water (both percents on a weight basis). A significant advantage of a crosslinked hydrogel wick is its ability to prevent the free flow of water to the solid phase, particularly to a porous solid phase such as a molecular sieve tablet, even when the source of water is above the tablet and exerts a head pressure on the wick. The reason is that diffusion rather than head pressure is the primary controlling factor for the water delivery rate through the wick.

Some wicks are more sensitive to head pressure effects. Accordingly, when the water source is above the tablet, the hydrostatic pressure of the water will add significantly to the driving force for the water flow rate. Examples of this type of wick include certain felt products, large open-cell sponge materials, such as viscose sponge materials, and porous plastic structures such as those made by Porex Technologies, Fairburn, Ga., USA. An example of a suitable felt material is SIF Felt type 6-900Z made by Foamex International, Inc., Eddystone, Pa., USA. An advantage to the use of felt wicks is that very fast flow rates can be obtained in certain orientations.

Other factors affecting the flow rate of water or other liquid into or toward the solid phase are the surface area of contact between the wick and the solid phase, the surface area of the wick exposed to the liquid reservoir, the liquid level in the liquid reservoir, the absorbent potential of the solid phase, and density of the solid phase. The greater the contact area between the wick and the solid phase, the faster the flow of water into the solid phase, although the relationship is not directly proportional. The cross sectional area of the wick has a large effect on flow rates, with larger cross sectional wicks having an enhanced ability to cause liquid to flow through them. If the liquid and solid phases are isolated in separate compartments, a pressure differential may develop between the compartments, causing a pressure gradient along the wick. This can reduce or arrest the flow of liquid through the wick. This effect can be eliminated by venting gas between the two compartments. Alternatively, the pressure differential can be used as a further means of controlling the wicking rate, by controlling the size or number of holes serving as the gas vent.

Another means of controlling the wicking rate is the addition to the wicking liquid of materials that raise the viscosity of the liquid. Examples of such materials are hydroxy ethyl cellulose, hydrogel forming polymers, and polyethylene glycol polymers, particularly for aqueous liquid phases. Additionally, hydrophilic and hydrophobic surfactants can be added to the wick, the liquid phase or both, to affect the flow rate. For aqueous liquids, hydrophilic surfactants will decrease the wicking rate by lowering the surface tension. A similar effect can be achieved by incorporating a viscosity increasing substance in the solid phase.

The wicking effect can also be achieved by wicking media rather than a discrete wick. An example of a nondiscrete wick is compacted superabsorbent polymer particles held together by a retaining structure. Superabsorbent polymer hydrates upon contact with water, and a hydrated superabsorbent polymer particle then hydrates other superabsorbent polymer particles in contact with it. Alternatively, the solid phase material itself can be used as a wicking material. When the solid phase is a molecular sieve tablet, for example, the tablet can be formed with a leg rather than a through hole for insertion of a discrete wick. The leg is thus made of compressed tablet material and acts as a wick.

Using a tablet again as an example, the tablet itself can serve as a wick, and placed in direct contact with the liquid phase. With the phases thus in direct contact, control over the wicking rate and gas release can be achieved by various means. As one example, the viscosity of the liquid phase can be increased by the inclusion of a suitable additive. One example of such an additive is hydroxyethylcellulose. Further description of this method appears below.

For aqueous liquids, unless the solid phase is directly immersed in the liquid, wicking does not require the use of a hydrophobic membrane to separate gas from liquid, since only gas is emitted from the solid phase. Excess liquid can be retained in the solid phase. Certain prior art devices require the use of a gas-liquid separation membrane for effective operation, since the evolution of gas bubbles occurs in the presence of free flowing liquid. Therefore, by its ability to function effectively with the liquid phase retained inside the solid phase, this invention represents a significant improvement over the use of hydrophobic membranes. When the solid phase is a molecular sieve tablet, the liquid phase is retained in the interstitial spaces between the molecular sieve particles that comprise the tablet. When the solid phase is a chemical species or combination of species that produce a solid residue when reacting with the incoming liquid to produce the gas, the reactants are replaced by the solid residue which retains the shape of the tablet. This ensures that the structure of the tablet is never fully compromised, allowing it to retain excess water. An alternative means of retaining the tablet shape as gas generation proceeds is by the inclusion of tableting agents, which can provide a stable insoluble framework.

In preferred embodiments of the invention, the solid phase is constructed and formulated to prevent liquid phase from flowing out of the solid phase after having entered it. If a peroxide/catalyst system as described below is used, the tablet consists in part of absorbent media, which prevents excess water from flowing out of the tablet. Similarly, once the absorbent media in a peroxide/superoxide tablet is fully hydrated, there is no longer a driving force to allow for further wicking of water solution. With molecular sieve tablets and chemical couplets, once the tablet is saturated with water, there is no longer a driving force available to continue the wicking effect. This self limiting action prevents any free liquid from entering into other parts of the infusion device.

Immersion Methods

As an alternative to the use of a wick to control the diffusive transport of the liquid phase toward the solid phase, control can also be achieved with the solid phase immersed in the liquid phase.

Gas adsorbed on molecular sieves, for example, can be desorbed at a controlled rate under certain conditions. If an untreated carbon dioxide loaded molecular sieve is submerged into pure water, the carbon dioxide is released over a period of about one to five mninutes. If a modified water bath is used rather than water itself, the desorption rate can be significantly decreased. Methods of modification include adding an inert solute to the water to serve as a diluent of the water, increasing the viscosity of the water, or both. Examples of inert solutes are polyalkylene glycols, particularly polyethylene glycol, preferably of a weight averaged molecular weight of from about 400 or to about 600 (PEG 400 and PEG 600). Any amount of PEG 400 or PEG 600 can affect the desorption rate, with concentrations over about 1% and less than 100%. Preferred concentration ranges are about 1% to about 90%, and about 20% to about 60%, all by weight.

The viscosity of water can be increased by the addition of a high-viscosity solute. Examples of such solutes are cellulose and cellulose derivatives. A specific example is hydroxyethylcellulose (HEC). A small amount (from about 0.1% to about 5% by weight) of HEC significantly increases the viscosity of water, and dramatically decreases the rate of desorption of carbon dioxide from a molecular sieve. With solutes of this type, the time required to release all carbon dioxide adsorbed on a molecular sieve tablet can be extended to 24 hours or more. This is useful in liquid infusion pumps in which long liquid infusion times are desirable.

When an uncoated molecular sieve tablet bearing adsorbed $CO_2$ is immersed in a solution of thickened or modified water, its flow rate starts high and gradually drops. This is due in part to the diffusion path of the water containing liquid into the tablet. Immediately after immersion, the entire outside surface area of the tablet is exposed to the solution, and this large surface area releases gas at an initially high rate. As the water diffuses deeper into the tablet, the effective surface area of contact, i.e., the area where incoming water contacts adsorbed gas, is reduced and the flow rate decreases. It is possible to achieve a more constant diffusion rate by coating a portion of the molecular sieve tablet with a water-repellent or water-impermeable coating. For tablets containing a central hole, a preferred method is to coat the entire surface of the tablet except for the central hole, and optionally the peripheral edge. The viscosity-modified water solution will then enter the central hole, migrate directly into the center of the tablet, and travel radially outward over time, producing a substantially constant gas desorption rate. This will produce a more level flow rate curve, while the tablet remains intact. Examples of water-impermeable coatings are hot melt adhesive, BLACK MAX™ sealant (Loctite Corporation, Newington, Conn., USA), synthetic rubber, and polyurethane.

When using immersion methods as described in this section, the inclusion of a hydrophobic porous membrane is often desirable to separate the evolved gas from the liquid. The evolved gas can then be used to drive the liquid infusion device without regard to orientation of the device. Various hydrophobic membranes capable of serving this function are known to those skilled in the art.

Sorbent Materials

In certain embodiments of the invention, gas is generated by the desorption of gas from sorbent materials on which the gas is adsorbed. Carbon dioxide and other gases can be loaded (adsorbed) onto various sorbents, examples of which are zeolite molecular sieves (both naturally occurring and synthetic), carbon molecular sieves, silica gel, activated carbon. Zeolite molecular sieves and mixtures of zeolite molecular sieves are preferred. Linde type 13X, Linde type Y, Linde type 4A and Linde type 5A zeolite molecular sieve materials (UOP, Tarrytown, N.Y., USA) are examples of adsorbents that can be used in the practice of this invention. These adsorbents and their manufacture are disclosed in U.S. Pat. Nos. 2,882,244 (for zeolite type X molecular sieves), 2,882,243 (for zeolite type A molecular sieves), and 3,130,007 (for zeolite type Y molecular sieves). Methods for forming these materials into bodies such as tablets, beads or pellets are disclosed in U.S. Pat. Nos. 3,888,998, 3,992,493, and 4,007,134.

Zeolite molecular sieve sorbents can be loaded with carbon dioxide gas up to a maximum of about 25% by weight carbon dioxide, based upon the initial unloaded weight of the molecular sieve. Zeolite type 13X typically holds the most carbon dioxide. Zeolite type 4A can hold about 60% to 70% of the carbon dioxide loading of Zeolite type 13X, but is capable of desorbing the gas at a significantly slower rate than 13X, which is useful in certain cases. Zeolite type Y is similar to type 13X in its capacity for carbon dioxide.

Zeolite molecular sieves materials should be very dry, preferably with a water content below about 2% by weight prior to adsorbing gas thereto. The zeolite molecular sieves as received from manufacturers generally meet this requirement. If drying (activating) the molecular sieve is desired or necessary, this can be accomplished by methods disclosed in U.S. Pat. Nos. 3,888,998, 3,992,493, and 4,007,134. These materials can also be dried by exposure to reduced pressure at low temperatures. Microwave energy can also be used to accelerate the rate of drying. Dry zeolite molecular sieve is loaded with carbon dioxide gas by means of placing the molecular sieve in a pressure vessel with carbon dioxide gas. Alternately, carbon dioxide gas can be passed through a packed column of the molecular sieve. Methods of charging the molecular sieves with carbon dioxide are disclosed in the above-mentioned patents, and are well known to those skilled in the art. Once gas is adsorbed onto the molecular sieve, it will remain adsorbed during storage, provided that the molecular sieve is contained in a barrier container to protect it from environmental gases, moisture or water.

Molecular sieves are available in various physical forms, including pellets, beads, and powders. The preferred form of zeolite molecular sieves for the purposes of this invention is the powdered form. A preferred sorbent for use with this invention is a mixture of Linde Zeolite type 13X molecular sieve (about 0% to 100% of the molecular sieve content by weight, preferably about 55% if needed), Linde Zeolite type 4A molecular sieve (about 0% to about 100% of the molecular sieve content by weight, preferably about 45% if needed), short hydrophobic fibers, such as polypropylene or polyester fibers (about 1 to 10% by weight), and a tablet lubricant, such as magnesium stearate (about 1% to about 8% by weight). These materials are mixed, then formed into tablets by compression. In a presently preferred practice, the components are pressed into a tablet about 1.375 inches (3.5 cm) in diameter and about 0.76 inch (1.9 cm) thick, preferably with a small hole (about 0.0625 inch, 0.16 cm, in diameter) in the center of the tablet. The cylindrical hole in the tablet serves to hold a wick in place.

Various gases can be used as alternatives to carbon dioxide. Refrigerant gases, for example, can be used, such as 1,1,2-trifluoroethane. The weight of adsorbed gas required to achieve a given volume of evolved gas is proportionate to the molecular weight of the gas. Unfortunately, most low molecular weight gasses, such as helium, oxygen, argon, and nitrogen, adsorb in quantities that are too small at room temperature to be useful. Flammable gases can also be used, although their flammability may be objectionable in many applications. Ammonia gas is a further alternative, offering a lower molecular weight than carbon dioxide and a high level of adsorption to the molecular sieve. In some applications, however, the ammonia odor may be objectionable.

Tablets made from molecular sieve and other sorbent materials can be regenerated after having been depleted of adsorbed gas. It is only necessary to dry out (activate) the depleted sorbent and reload it with fresh gas to prepare the sorbent for a subsequent use. If activation is achieved by the use of a reduced pressure and modest temperatures, the sorbent can be regenerated while still in an infusion device.

In this specification and the appended claims, the term "solid phase" includes solid materials as well as solid materials with gas molecules adsorbed onto the surface of the solid.

Gas Generating Compositions

Various compositions can be used to generate gas in accordance with this invention. One class of compositions is the combination of a base and an acid to produce carbon dioxide. The acid and base are combined in dry form and rendered reactive only when codissolved in water. Examples of suitable bases are water-soluble carbonate and bicarbonate salts, nonlimiting examples of which are sodium bicarbonate, heat treated sodium bicarbonate, sodium carbonate, magnesium carbonate, potassium carbonate, and ammonium carbonate. Nonlimiting examples of suitable acids are citric acid, tartaric acid, acetic acid, and fumaric acid. One presently preferred composition is a dry mixture of sodium bicarbonate and fumaric acid. Compositions containing more than one acid component or base component can also be used.

The rate of gas generation can be controlled by the solubility of one or both of the chemicals in water. In wick and tablet systems, the available water as delivered by the wick to the tablet dissolves only a limited amount of the reactants and resulting reaction product(s). The reaction is thus limited by the solubility of the chemicals in the limited amount of available water. The rate of water delivery thereby controls the reaction rate. Some examples of the solubility of suitable reaction chemicals per 100 grams of water are as follows: sodium bicarbonate, about 10 g; citric acid, about 200 g; tartaric acid, about 20 g; and fumaric acid, about 0.7 g. The limited solubility and limited water delivery rate through the wick make it unnecessary to keep the acid and base separated either before or during use of the infusion device.

As a manufacturing aid, it may be desirable to add inert agent(s) to the reactant composition to aid in the tableting process and to keep the tablet intact during and after use. Examples of suitable tableting aids are polyvinyl pyrrolidone and anhydrous dibasic calcium phosphate, sold by Edward Medell Co. (Patterson, N.J., USA) as EMCOMPRESS®. Tableting aids can be eliminated for certain compositions with no loss of performance. one such composition is the mixture of sodium bicarbonate and fumaric acid.

Chemical compositions that produce oxygen or other gases can also be used. A composition to generate oxygen in the presence of water is disclosed in U.S. Pat. No. 4,405,486. The controlled rate of wicking water into such a tablet, and the limited solubility of the constituents can control the rate of oxygen release in a manner similar to that of carbon dioxide in the systems described above.

Peroxide and Superoxide Chemical Systems

In certain embodiments of this invention, gas is generated by drawing an aqueous solution of a peroxide or superoxide into an absorbent tablet that contains an enzyme or catalyst which promotes the decomposition of the peroxide or superoxide to decomposition products including oxygen gas. Alternatively, a solid peroxide or superoxide can be incorporated into the tablet, with oxygen generation being initiated by contact of the peroxide or superoxide with water. Hydrogen peroxide, for example, decomposes into water and oxygen, providing no hazardous reaction products after infusion of the liquid has been completed. Metal peroxides, such as lithium peroxide, sodium peroxide, magnesium peroxide, calcium peroxide, and zinc peroxide, react with water to produce the metal hydroxide and hydrogen peroxide, which then decomposes into water and oxygen. Superoxides, such as sodium superoxide, potassium superoxide, rubidium superoxide, cesium superoxide, calcium superoxide, and tetramethylammonium superoxide, react with water to produce the metal hydroxide and oxygen gas directly. Hydrogen peroxide itself is particularly preferred.

A suitable tablet contains a water absorbent material to facilitate the wicking action, and the enzyme or catalyst in systems where enzymes or catalysts are used. Examples of water absorbents useful for this purpose are superabsorbent polymers, reconstituted cellulosic materials and compressed zeolite powder (Types 13X and 4A, both unactivated).

One example of a suitable enzyme is catalase, with lyophilized catalases preferred. Catalysts effective for the decomposition include metals deposited on high surface area substrates such as alumina or activated carbon. Examples of suitable catalysts are platinum, palladium, and silver.

Chemical reactants can also be used rather than enzymes or catalysts to decompose hydrogen peroxide. Examples of such reactants are potassium permanganate and sodium hydroxide. These are often less preferred, however, due to safety concerns.

Among enzymes and catalysts, enzymes provide a cost benefit for single-use systems. For reusable systems, however, catalysts are preferred. A significant advantage to the use of a hydrogen peroxide system with a catalyst is the ability to regenerate the system. This is done by drying out the tablet and adding more hydrogen peroxide solution to the water reservoir. Regeneration in this system is thus easier than regeneration of a sorbent tablet for a system that requires adsorbed gas.

Formation of a Tablet

Tablets for use in the present invention can be prepared by conventional techniques. A preferred method is one in which the tablet components are placed in a die, then pressed to form a shaped tablet. This method is known as direct compaction and the procedures are well known to those skilled in the art. To prepare a tablet with a central hole to receive a wick, the hole can be formed during the pressing operation, or drilled into the tablet after the tablet is formed.

The specific gravity of the pure Type 13X molecular sieve is about 2.0 g/cm$^3$. The density of a pressed tablet made from this material is about 1.5 g/cm$^3$. The difference is attributable to porosity in the tablet, in the form of microscopic cavities or interstitial spaces between the molecular sieve particles. This porosity permits capillary diffusion of water or other liquid throughout the tablet. The pressure at which the tablet is pressed determines the relative porosity of the tablet. To achieve a density of about 1.5 g/cm$^3$, about 40,000 pounds of force ($1.8 \times 10^5$ newtons) are needed. A density of about 1.5 g/cm$^3$ is preferred for molecular sieves in order to maximize the amount of gas adsorbed to the molecular sieve.

For tablets containing a combination of reactant materials, the ingredients are mixed together and then tableted in a similar manner to that stated above. The amount of pressure applied during tablet formation effects the density, which in turn affects the water ingression rate from the wick. For the hydrogen peroxide system, the tablet need only contain the enzyme and absorptive tableting filler. The same tableting technique can be used to create this type of tablet as well.

Structure of the Infusion Device

Certain structural features of the infusion device affect its performance, and can be optimized by the use of preferred materials and methods of construction.

The beneficial liquid to be dispensed by the infusion device is retained in a bladder, which term is used herein to denote any liquid-impermeable pouch or enclosure that is sufficiently flexible to be compressed, preferably to an extent sufficient to substantially eliminate its internal volume.

The pressure containment pouch, or housing of substantially gas-impermeable wall material that surrounds the bladder that contains the beneficial liquid to be dispensed, is preferably flexible yet substantially nonextensible. A preferred construction is one consisting of a seamless extrusion of soft, flexible plastic, such as plasticized polyvinyl chloride, to form an inner lining, laminated to an outer flexible, but substantially nonextensible plastic such as oriented polyester. Examples of oriented polyester are MYLAR® Type A and Type D (E.I. Du Pont de Nemours Co., Wilmington, Del., USA). The MYLAR can be applied over the vinyl tubing on a mandril, and bonded to the vinyl by application of use of a pressure-sensitive adhesive and the application of pressure. Alternatively, the two layers can be flexible and rigid polyvinyl chloride, respectively. Laminated tubes can also be formed by co-extrusion, or from flat, multi-layer film or sheeting by adding a seam. The advantage of a laminated tube is that both flexibility and avoidance of distension due to internal pressure can be achieved with a thin total wall thickness. Although the thickness can vary, a preferred range for the inner lamina thickness is from about 0.01 cm to about 0.05 cm, and a preferred range for the outer lamina thickness is from about 0.001 cm to about 0.005 cm. in a presently preferred embodiment, the inner lamina is a polyvinyl chloride tube 0.010 inch (0.0254 cm) in thickness (LAYFLAT, Solvay Draka B.V., Enkhuizen, The Netherlands), and the outer lamina is MYLAR Type D polyester 0.001 inch (0.00254 cm) in thickness or an oriented polyester with pre-applied pressure sensitive adhesive (PROTEKT™ Overlaminating Film, Item 14, Madico Incorporated, Woburn, Mass., USA, about 0.001 inch (0.00254 cm) in thickness).

An advantage of a flexible pressure containment pouch for retaining pressure is its ability to be stored in a folded and/or collapsed configuration to save space. Also, this type of composite structure can be made of optically clear material, which is advantageous for the purpose of monitoring the amount of liquid remaining to be infused, and to permit inspection of the pouch to detect the presence of impurities.

The avoidance of excessive pressure within the pressure containment pouch and the maintenance of a steady flow rate of liquid from the infusion device is achieved by a pressure relief valve. Typical running pressures of pressure infusion devices are in the range of about 7 PSIG to about 10 PSIG ($4.8 \times 10^4$ to $6.9 \times 10^4$ pascals). Either a fixed-pressure or a variable-pressure relief valve can be used. In devices containing a single-pressure relief valve, a valve that relieves pressure at approximately 10 PSIG is preferred. A variable-pressure relief valve which ranges from, for example, 5 PSIG to 15 PSIG ($3.4 \times 10^4$ to $1.0 \times 10^5$), will accommodate wide range of flow rates with a single infusion set, since flow is directly proportional to the pressure in the device. Accordingly, a variable-pressure relief valve with such a range will be particularly usefull in this invention.

One method of producing a pressure relief valve is to stretch a section of elastomeric tubing or sleeve over a protruding lug or stem in sealing relationship, the sleeve and stem constructed in such a manner that the pressurized gas region of the pressure containment pouch is in communication with the contacting surface between the sleeve and stem. The sleeve will then be separable from the stem when the pressure in the pouch exceeds a threshold gas pressure. To permit adjustment of the cracking (relief) and reseat pressure of the valve to a desired value, the stem can be slightly tapered. The elastomeric sleeve can then be moved along the taper of the tube to increase or decrease the hoop stress in the elastomeric sleeve, which will in turn increase or decrease the cracking pressure. A preferred sleeve material is a low tensile-set elastomeric material. Synthetic silicone rubbers are preferred, with poly(methyl vinyl siloxane) the most preferred, although other materials can also be used.

The use of a lubricant which also functions as an anti-blocking agent further enhances the adjustability of the device. The lubricant can be applied to the contacting surfaces of sleeve and stem to avoid a high initial cracking pressure due to blocking over time. Examples of lubricants suitable for this purpose are white petrolatum (VASELINE® Petroleum Jelly, Chesebrough-Ponds, Inc., Greenwich, Conn., USA), fluorinated silicone oils, mineral oil, fumed silica, and mixtures containing one or more of these constituents.

A pressure relief valve of this construction and including an anti-blocking lubricant provides close control of cracking and reseat pressures, and produces cracking and reseat pressures that are close to each other in value to achieve a substantially constant pressure within the device.

A further feature preferably included in infusion devices in accordance with this invention is a starting mechanism to permit safe storage of the infusion device without gas evolution for an extended period of time, and to provide a convenient means of starting the gas evolution when desired. These results can be accomplished by using a wick that is preinserted into a central hole in the solid phase tablet, while the free end of the wick is placed in a movable shroud within a chamber of the infusion device that contains the liquid phase. When the start of gas evolution is desired, the shroud can be pulled back, exposing the dry end of the wick to the liquid phase and starting the wicking action and hence the liquid flow.

An alternative is to encase the wick in a frangible shroud which can be shattered immediately prior to use of the device, exposing the wick to the liquid phase. In a further alternative, the liquid phase is injected through a port immediately prior to use of the device. A still further alternative is to encapsulate the liquid phase in one or more frangible containers. Upon rupture of these containers, a liquid reservoir in the device is filled with the liquid which is then free to contact the wick. A still further alternative is to place a flexible tubular barrier film with integral tear strip(s) over the wick. The tear strips are pulled to expose the wick to the liquid phase. Other methods of starting and equivalents of these methods will be readily apparent to those skilled in the art.

Examples of infusion devices in accordance with this invention and their component parts are shown in the attached Figures.

Figure 1:
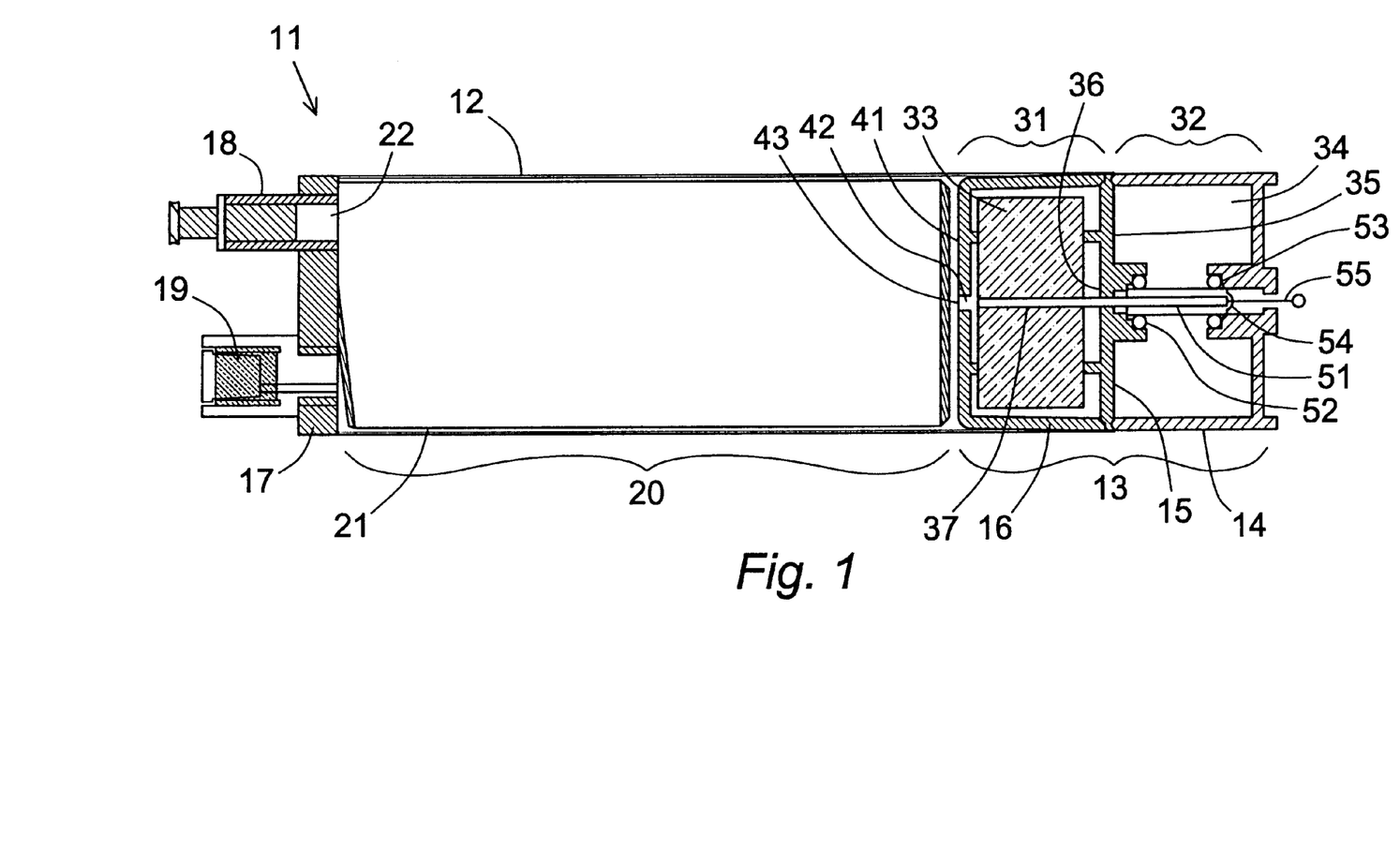
FIG. 1 is a side elevation view in cross section of an infusion device in accordance with the present invention.

FIG. 1 illustrates an infusion device 11 constructed of a housing 12 or pressure containment pouch of flexible, substantially nonextensible (i.e., substantially nondistendable) tubing material, sealed at one end by a rigid compartmented base assembly 13 formed from three pieces 14, 15, 16 of a material such as rigid polyvinyl chloride (PVC) welded together by conventional means, such as ultrasonic welding. The housing 12 is sealed at the other end by a cap 17 that contains a fitting 18 for passage of the liquid that is being dispensed, and a pressure relief valve 19. Inside the housing 12, between the base assembly 13 and the cap 17 is a cavity 20 in which the bladder 21 containing the beneficial liquid resides.

The bladder is fully closed except for a single opening 22, and is joined to the housing 12 around this opening in a sealing engagement. The bladder is thus free to compress within the cavity 20 as the gas pressure in the housing 12 rises, whereupon the contents of the bladder will be expelled through the opening 22 and out of the housing through the fitting 18. The bladder may be constructed with internal ribs to ensure an open passageway at all times for the beneficial liquid to flow through and out of the bladder. The capacity of the bladder 21 is not critical to the invention, and can vary. In one presently preferred embodiment, the bladder has a capacity of 100 mL when filly expanded to fill the cavity 20. The fitting 18 can be a LUER-LOK® (Becton-Dickinson Corporation, Franklin Lakes, N.J., USA) type fitting, which preferably contains a syringe-activated check valve.

The base assembly 13 forms two compartments 31, 32, one 31 to house the solid phase 33 and the other 32 the liquid phase 34. The wall section 35 separating the two compartments contains a single hole 36 that communicates the interiors of the two compartments, and a wick 37 passes through the hole 36, joining the solid and liquid phases. The solid phase 33 is represented in this Figure by a tablet with an axial hole through which the wick 37 is inserted. A typical tablet is a composite consisting of about 7.4 g of zeolite molecular sieve Type 13X, about 9 g of zeolite molecular sieve Type 4A, about 0.34 g of natural polyester fibers, and about 0.17 g of magnesium stearate. A typical wick is made of crosslinked (acetalized) polyvinyl alcohol.

The wall section 41 separating the tablet compartment 31 from the bladder cavity 20 has a gas outlet hole 42 passing through its center to permit the gas evolved from the tablet to pass into the region of the cavity 20 surrounding the bladder. In this particular construction, the gas outlet hole 42 is about 0.25 inch (0.6 cm) in diameter and is covered with a metallized barrier tape 43 held in place by a low-tack adhesive to render the tape easily removable. This protective tape serves as a barrier protecting the sorbent tablet from atmospheric moisture in the bladder cavity 20, and also prevents premature gas desorption from the sorbent tablet during storage (in embodiments where gas is generated by desorption). Upon initiation of use of the device, the barrier tape 43 is separated from the wall by the initial gas pressure generated in the base assembly.

Premature contact between the liquid and solid phases is prevented by various structural devices. One such device is a shroud 51 shown in FIG. 1, surrounding the portion of the wick 37 that extends into the liquid phase chamber 32. The shroud 51 is a length of rigid tubing, such as a molded PVC or high-density polyethylene tube, closed at one end and held in place by a pair of O-ring seals 52, 53. The closed end of the shroud has an integral eyelet 54 to which a pull string 55 (such as looped nylon) is attached. To place the wick 37 in contact with the liquid phase, the pull string 55 is pulled to draw the shroud back, thereby allowing the surrounding liquid to contact the wick.

Figure 2:
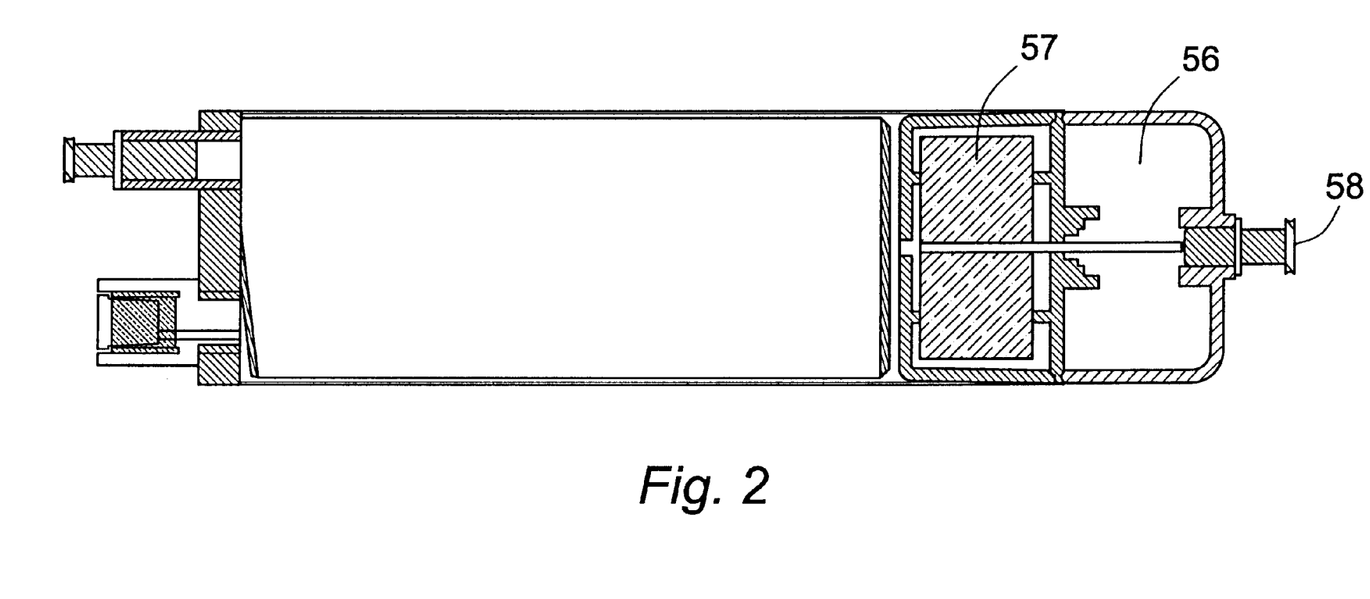
FIG. 2 is a side elevation view in cross section of a second infusion device in accordance with the present invention.

An alternative structural device and mechanism for withholding contact of the wick with the liquid phase until the desired point in time is shown in FIG. 2. Here, the liquid phase compartment 56 is empty when the infusion device is not in use, with only the solid phase tablet 57 contained within the device. A syringe-activated check valve 58 is incorporated in the outer wall of the liquid phase compartment 56, and at the appropriate time, liquid is injected into the compartment by syringe.

Figure 3:
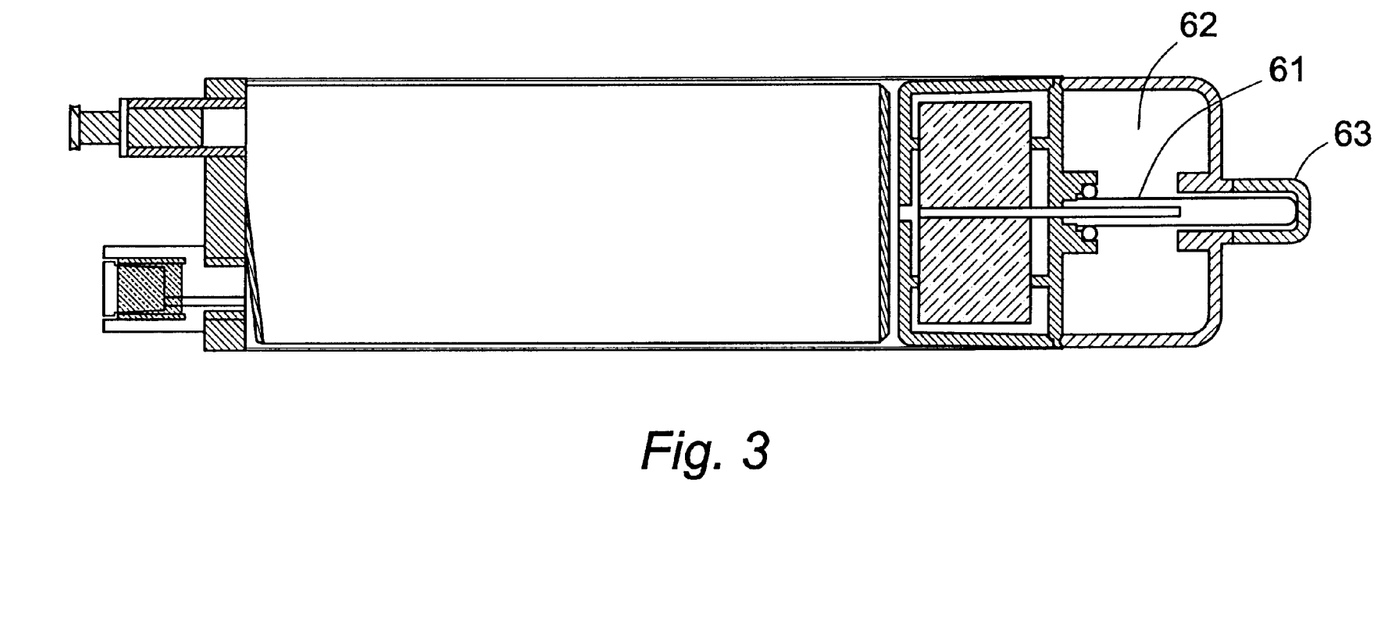
FIG. 3 is a side elevation view in cross section of a third infusion device in accordance with the present invention.

A third alternative is shown in FIG. 3, where the portion of the wick extending into the liquid phase chamber is surrounded by a frangible glass shell 61. The outer wall of the liquid phase compartment 62 contains a protruding section 63 of flexible material such as silicone. Contact of the liquid phase with the wick is initiated by squeezing the flexible protrusion 63 to break the glass shell 61.

Figure 4:
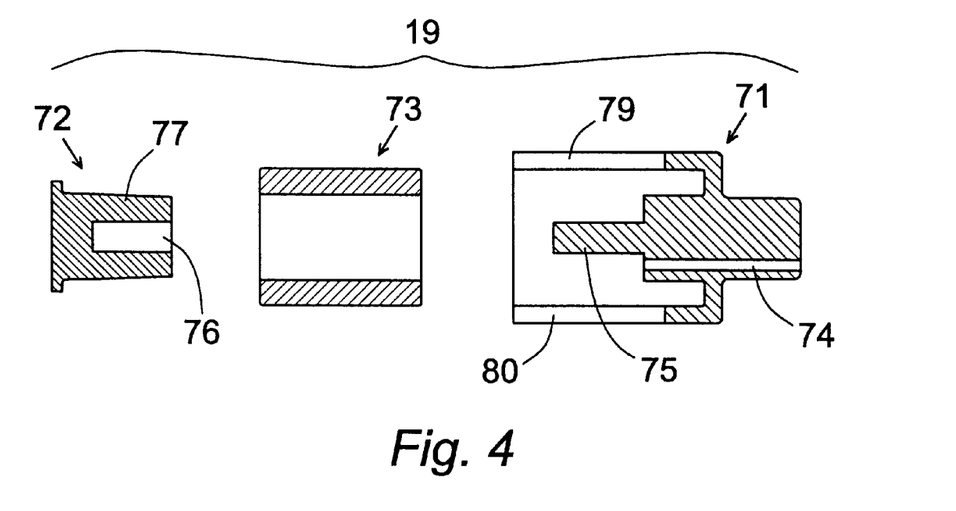
FIG. 4 is an exploded view in cross section of a pressure relief valve in accordance with the present invention.
Figure 5:
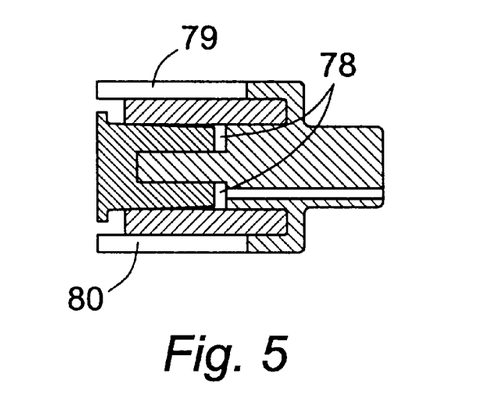
FIG. 5 is a similar view of the pressure relief valve of FIG. 4 with all parts assembled.

The pressure relief valve 19 is shown in exploded side cross section in FIG. 4 and in assembled side cross section in FIG. 5. The valve is constructed in three parts—a valve housing 71, a valve stem 72, and a sleeve 73. The valve housing 71 contains an inlet passage 74 that communicates with the region surrounding the bladder in the pressure containment housing 12 (FIG. 1) of the infusion device, and an internal pin 75. The valve stem 72 has a well 76 that fits tightly over the pin 75 in a secure manner that will not hold the stem in a fixed position through any pressures exerted inside the pressure containment housing. The sleeve 73 fits inside the valve housing 71 between the internal wall of the valve housing and the outer surface 77 of the stem. Pressure from the pressure containment housing is thus contained in the small enclosed volume 78 between the housing 71, stem 72 and sleeve 73. Lateral slits 79, 80 in the valve housing permit the sleeve to expand outward in response to high pressure, and thus to separate from the outer surface 77 of the valve stem 72 to relieve pressure. The outer surface 77 of the valve stem is tapered so that the contact force between the valve stem and the sleeve, and hence the cracking or relief pressure of the valve, can be varied by either moving the sleeve axially relative to the valve stem or moving the valve stem axially relative to the sleeve.

The following examples are offered solely for purposes of illustration.

EXAMPLE 1

Preparation of Composite Zeolite Molecular Sieve Tablet

This example illustrates the formation of rigid composite tablets with a density of about 1 $g/cm^3$.

12 grams of Sodium Aluminosilicate (Zeolite) Molecular Sieve Type 13X, 0.25 grams polyester fibers 0.040–0.060" length by 0.0025 inch diameter (type 9001 natural, Cellusuede Products Inc., Rockford, Ill., USA) and 0.12 grams of magnesium stearate are intensely mixed. This mixture is placed in a 1.375-inch diameter cylindrical tableting die. A punch placed in the dye is pressed against the powder using a hand-operated 20-ton Central Hydraulics hydraulic press. The mixture is compacted in the dye until a tablet height of approximately 0.6" is obtained. The newly formed tablet is removed from the die. Using a ⅛" diameter drill bit, a small hole is drilled into the center of the tablet. The tablet is then placed into a sealed container to protect it from atmospheric moisture.

EXAMPLE 2

Activating and Charging a Molecular Sieve Tablet

This example illustrates the method for loading the composite tablet of Example 1 with carbon dioxide.

Composite tablets are sealed inside a stainless steel pressure vessel from Pope Scientific. The pressure vessel is connected to a Marvac single stage high vacuum pump (Marvac Scientific Manufacturing Co., Concord, Calif., USA) and placed inside an air convection oven (Blue M STABILTHERM®, Blue M Electric, Watertown, Wis., USA). The vacuum pump remains outside of the oven. Tablets are then heated to 120–130 C. and exposed to a vacuum of about 29 inches of mercury. These conditions are maintained for 1.5 hours to dehydrate the tablets. The dehydrated tablets were then allowed to cool to room temperature while remaining under a vacuum. The hydrated tablets remained in the pressure vessel for 1.5 hours while carbon dioxide was introduced at a pressure of about 3–4 PSIG. After 1.5 hours, the vessel was sealed and the carbon dioxide-containing tablets were maintained under a carbon dioxide atmosphere for storage. Analysis of the carbon dioxide-containing tablets shows that they contain approximately 20% by weight carbon dioxide based on the change in weight of the type 13X zeolite molecular sieve.

EXAMPLE 3

Gas Desorption Using Polyvinyl Acetate Wick

This example illustrates the gas desorption process using a discrete polyvinyl acetate wick.

A tablet of the type described in Example 2 was used with a reservoir of distilled water. One end of a 70 mm×3 mm crosslinked polyvinyl acetate (PVAc) wick with a square cross section (Type CF120, Merocel Corporation, Mystic, Conn., USA) was inserted in the center hole of the tablet with one end of the wick flush with the upper surface of the tablet. The other end of the wick was placed in a reservoir containing 20 mL of distilled water. The resulting release of carbon dioxide was measured with an Aalborg Instruments rotameter (Aalborg Instruments & Controls Inc., Monsey, N.Y., USA). The resulting gas desorption rates are shown in Table 1 below.

TABLE 1

Rate of Desorption

| Time (minutes) | Outward Flow of Desorbed $CO_2$ (mL/min) |
|---|---|
| 2 | 59 |
| 5 | 4.6 |
| 11 | 1.6 |
| 20 | 1.1 |
| 30 | 1.0 |
| 40 | 1.0 |
| 50 | 1.0 |
| 60 | 1.0 |

The data in Table 1 indicates that without any type of rate modifying techniques, the tablet will desorb the carbon dioxide in a very short period of time.

EXAMPLE 4

Gas Desorption Using Slower Wicks

This example illustrates the effect of using different types of wick materials on the desorption rate of gas from the tablet.

Composite tablets prepared using the process described in Examples 1 and 2 underwent gas desorption using the method described in Example 3, each with different wick material. The wicks employed were a hydrogel (2ND SKIN® Non-stick Moist Burn Pads, Spenco Medical Corporation, Haywards Heath, United Kingdom) and an acetalized polyvinyl alcohol wick, type D-2 from Kanebo Ltd., Osaka, Japan (PVA-D-2). The flow of carbon dioxide out of each tablet was measured over time and the results are shown in Table 2.

TABLE 2

Rate of Desorption

| Time (minutes) | Outward Flow of Desorbed $CO_2$ (mL/min) | |
|---|---|---|
| | Hydrogel | PVA-D-2 |
| 1 | 6.74 | 104 |
| 5 | 2.47 | 92 |
| 10 | 1.51 | 65 |
| 20 | 1.36 | 20 |
| 30 | 1.47 | 13 |
| 40 | 1.70 | 7 |
| 50 | 1.95 | 6 |
| 60 | 2.10 | 6 |

Both wick materials provide transport of the water, but the PVA-D-2 produces a higher rate of gas release which indicates that it transports water at a higher rate.

EXAMPLE 5

Use of Infusion Device With $CO_2$-Loaded Zeolite

This example illustrates the method of using a composite zeolite tablet loaded with carbon dioxide to generate gas to run an infusion device.

Twelve (12) grams of zeolite molecular sieve type 13X (from UOP, Tarrytown, N.Y., USA) was mixed with 0.12 grams of magnesium stearate and 0.25 grams polyester fibers 0.040–0.060 inch in length by 0.0025 inch in diameter (type 9001 natural, CellCellusuede Products Inc., Rockford, Ill., USA) and prepared into a tablet using the procedures of Example 1. The tablet was then placed in a device of the construction shown in FIG. 2.

To start the device, a 25-cc syringe was used to inject 12 grams of distilled water into the wicking liquid reservoir of the device. The infusion device utilized a 0.078"× 0.078"× 1.6" crosslinked polyvinyl acetate wick (PF120 of Merocel Corporation, Mystic Conn., USA). Immediately after the injection of the distilled water, the water started to enter the tablet.

The carbon dioxide desorbed from the tablet pressurized the rigid housing of the infusion device, causing the water in the medication pouch to flow. The pressure relief valve of this device was set to release excess gas at a pressure of 10 PSIG.

The pressure and volumetric flow rates were monitored over time using a pressure gauge and graduated cylinder and were recorded in Table 3 below:

TABLE 3

Infusion Pressure and Liquid Delivery Rate

| Time (minutes) | Infusion Pressure (PSIG) | Cumulative Delivered Liquid Volume (mL) |
|---|---|---|
| 1 | 3 | <10 |
| 2 | 9 | <10 |
| 3 | 10 | <10 |
| 5 | 10 | 12 |
| 7 | 10 | 14 |
| 9 | 10 | 17 |
| 10 | 10 | 19 |
| 12 | 10 | 22 |
| 14 | 10 | 26 |
| 15 | 10 | 28 |
| 19 | 9.5 | 36 |
| 22 | 9.5 | 42 |
| 25 | 8 | 48 |
| 26 | 8 | 49 |
| 27 | 8 | 51 |
| 28 | 7.5 | 53 |
| 29 | 7.5 | 54 |
| 30 | 7 | 55 |
| 35 | 6 | 62 |
| 40 | 6 | 69 |
| 45 | 5 | 76 |
| 50 | 5 | 80 |
| 55 | 4 | 86 |
| 60 | 4 | 90 |

The data in Table 3 demonstrate that an infusion device can be run using a wick combined with a composite zeolite tablet loaded with carbon dioxide.

EXAMPLE 6

Use of a Wick to Transport $H_2O_2$ Solution to a Catalyst-Impregnated Tablet

This example illustrates the use of a wick to transport hydrogen peroxide solution to a tablet with an impregnated catalyst to generate gas to run an infusion device.

Five (5) grams of 20×50 mesh activated high surface area carbon coated with 3% by weight palladium catalyst was mixed with 0.05 grams of magnesium stearate, 0.10 polyester fibers 0.040–0.060" in length by 0.0025 inch in diameter (type 9001 natural, Cellusuede Products Inc., Rockford, Ill., USA), 3.4 grams of zeolite molecular sieve type 4A and 1.4 grams of zeolite molecular sieve type 13X. This mix was formed into a tablet using the tablet pressing procedures described in Example 1. The zeolite materials were not activated or loaded with gas in this example, and were present only for the purpose of creating a tablet to hold the catalyst.

An 8% (by weight) hydrogen peroxide solution was then prepared by diluting a 35% hydrogen peroxide solution with distilled water. This solution was injected into the wicking reservoir of the infusion device using a 25-cc syringe. The device contained a 0.078"×0.078"×1.6" acetalized polyvinyl alcohol grade E-2 wick from Kanebo Corporation. The hydrogen peroxide solution was drawn into the tablet over a period of time, initiating the release of oxygen gas.

In this case the gas was generated within a rigid PVC power pack assembly, and transported by a tubing connection to a 250-mL rigid infusion device which has a gas side and a liquid side separated by a dual membrane system, in a rolling diaphragm configuration. As the gas side of the device expands, the diaphragm rolls into the liquid side of the device, expelling the liquid contents. Distilled water was used as the infusion liquid. The oxygen generated from the decomposition of the hydrogen peroxide pressurized the gas side of the infusion device, causing the distilled water to flow out of the device. A pressure relief valve was used to vent gas from the gas portion of the device when the internal pressure of the device exceeded about 10 PSIG. An infusion tubing set calibrated for 5% dextrose solution, viscosity expected to be 10–15% greater than test solution, to deliver 100 mL/h of liquid at 10 PSIG was connected to the device.

The gas pressure and volumetric flow rates were monitored over time using a standard laboratory pressure gauge and graduated cylinder and are shown in Table 4.

TABLE 4

Infusion Pressure and Liquid Delivery Rate

| Time (min) | Infusion Pressure (PSIG) | Cumulative Delivered Liquid Volume (mL) |
|---|---|---|
| 1 | 2.5 | <10 |
| 2 | 4.5 | <10 |
| 3 | 6 | <10 |
| 4 | 7.6 | 6 |
| 5 | 9 | 7 |
| 10 | 10.3 | 17 |
| 15 | 10.3 | 28 |
| 20 | 9.1 | 38 |
| 25 | 8 | no reading |
| 30 | 7.5 | 53 |
| 35 | 8.5 | 62 |
| 40 | 8.1 | 71 |
| 45 | 7.9 | 77 |
| 50 | 7.5 | 84 |
| 55 | 7.9 | 89 |
| 60 | 7 | 95 |

The data in Table 4 demonstrates that an infusion device can be powered by wicking a peroxide-containing liquid into a tablet which is impregnated with a catalyst.

EXAMPLE 7

Use of Acetalized PVA Wick to Transport Water to Sodium Carbonate/Citric Acid Tablet This example illustrates the method of using an acetalized polyvinyl alcohol wick to transport a limited amount of water to a tablet containing sodium bicarbonate and citric acid for the purpose of generating carbon dioxide gas in a controlled manner.

Sodium bicarbonate (8.6 g) was mixed with citric acid (5.7 g), fumed silica (1 g, AEROSIL® 200 from Degussa Corp., Ridgefield Park, N.J., USA), polyvinyl pyrrolidone (0.75 g, Type K-90 from ISP Technologies, Inc., Wayne, N.J., USA) and natural polyester fibers (0.75 g), 0.040–0.060 inch in length by 0.0025 inch in diameter (Type 9001 natural, Cellusuede Products Inc.). This mix was formed into a tablet using the tablet forming procedures of Example 1.

Through the tablet was placed a 0.078"×0.078"×1.6" acetalized polyvinyl alcohol wick (Grade E from Kanebo). The tablet was placed in a rigid PVC infusion device assembly. The wick was extended into a water reservoir in the assembly filled with distilled water. The rigid PVC assembly also contained a pressure relief valve set to vent gas at pressures above about 10 PSIG. The carbon dioxide gas generated from the controlled reaction of the citric acid and sodium bicarbonate was then used to power an infusion device as described in Example 6, with liquid being delivered through a 100 mL/h administration set calibrated for a 5% dextrose solution, viscosity expected to be 10–15% greater than the test solution.

The pressure and volumetric flow rates were monitored over time and were recorded in Table 5.

TABLE 5

Infusion Pressure and Liquid Delivery Rate

| Time (min) | Infusion Pressure (PSIG) | Cumulative Delivered Liquid Volume (mL) | Time (min) | Infusion Pressure (PSIG) | Cumulative Delivered Liquid Volume (mL) |
|---|---|---|---|---|---|
| 1 | 1.5 | 2 | 70 | 9.3 | 100 |
| 2 | 7 | 3 | 75 | 9.5 | 106 |
| 3 | 10 | 5 | 80 | 9.5 | 111 |
| 4 | 10.2 | 6 | 85 | 9.5 | 116 |
| 5 | 10 | 7 | 90 | 9.5 | 119 |
| 10 | 9.5 | 17 | 100 | n/a* | n/a |
| 15 | 9 | 25 | 110 | 9.5 | 131 |
| 20 | 8.5 | 32 | 120 | 9.5 | 138 |
| 25 | 8 | 40 | 130 | 9.3 | 155 |
| 30 | 8 | 47 | 140 | 9.1 | 174 |
| 35 | 8 | 53 | 150 | 9.1 | 192 |
| 40 | 8.8 | 60 | 160 | 9.3 | 210 |
| 45 | 9 | 68 | 170 | 9.3 | 229 |
| 50 | 9 | 76 | 180 | 9.5 | 243 |
| 55 | 9 | n/a | 190 | 9.5 | 256 |
| 60 | 9.1 | 88 | 200 | n/a | n/a |
| 65 | 9.1 | 94 | | | |

*"n/a": data not recorded

The results of this example demonstrate that an infusion device can be powered for an extended period of time by the controlled generation of carbon dioxide gas by wicking a limited amount of water into a tablet containing a mixture of sodium bicarbonate and citric acid.

EXAMPLE 8

Use of Acetalized PVA Wick to Transport Citric Acid Solution to Solid Sodium Carbonate This example illustrates the use of a wick made of acetalized polyvinyl alcohol to transport a citric acid solution into a sodium bicarbonate-containing tablet for the purpose of generating carbon dioxide gas in a controlled manner to power an infusion device.

Sodium bicarbonate (10 g) was mixed with polyvinyl pyrrolidone (1 g, Type K-90 from ISP Technologies) and polyester fibers (1 g) 0.040–0.060 inch in length by 0.0025 inch in diameter (Type 9001 natural, Cellusuede Products Inc.). This mix was formed into a tablet using the general procedures of Example 1.

A 2.6 molar solution of citric acid solution was prepared by dissolving citric acid into distilled water. A 12-mL portion of this solution was placed into the wicking liquid reservoir of a PVC assembly. A 0.078"×0.078"×1.6" acetalized polyvinyl alcohol wick (Grade E from Kanebo) was placed through the hole in the tablet. The citric acid wicking solution was allowed to wick into the tablet by placing the free end of the wick into the water reservoir. The carbon dioxide generated by the controlled reaction of the citric acid and sodium bicarbonate was used to power a 100-mL capacity infusion device, with liquid being infused through a 100 mL/h set calibrated for a 5% dextrose solution, viscosity expected to be 10–15% greater than the test solution. The infusion device was similar in construction to that described in Example 7. Again, a pressure relief valve with a setting of about 10 PSIG was used to vent excess gas from the system.

The pressure and volumetric flow rates were monitored over time and were recorded in Table 6:

TABLE 6

Infusion Pressure and Liquid Delivery Rate

| Time (min) | Infusion Pressure (PSIG) | Cumulative Delivered Liquid Volume (mL) |
| --- | --- | --- |
| 1 | 5 | 2 |
| 2 | 10.5 | 4 |
| 3 | 10.5 | 6 |
| 4 | 10.2 | 8 |
| 5 | 10.2 | 10 |
| 10 | 10 | 20 |
| 15 | 10 | 29 |
| 20 | 10 | 39 |
| 25 | 10 | 48 |
| 30 | 10.2 | 56 |
| 35 | 10.2 | 65 |
| 40 | 11 | 75 |
| 45 | n/a | n/a |
| 50 | 8.5 | 93 |
| 55 | 8 | 100 |
| 60 | 7.5 | 105 |

EXAMPLE 9

Use of Wick Enclosed in Frangible Shell

This example illustrates the use of a breakable shell as an alternative method to start an infusion device powered by desorption of carbon dioxide from a composite zeolite molecular sieve tablet.

A mixture (16.5 g) of 55% by weight zeolite type 4A and 45% by weight zeolite type 13X molecular sieve, was mixed with magnesium stearate (0.17 g) and polyester fibers (0.34 g) 0.040–0.060 inch in length by 0.0025 inch in diameter (Type 9001 natural, Cellusuede Products Inc.). The mixture was formed into a carbon dioxide loaded tablet using the procedures of Example 1 and Example 2.

The tablet was placed in a three-piece rigid PVC assembly, as shown in FIG. 3. One piece of the assembly served as the housing for tablet. The second piece served as a reservoir for wicking liquid (distilled water in this case). The two sections were separated by a round disk with a central hole for the wick to pass through. One end of an acetalized polyvinyl alcohol wick was placed through the tablet, and the other end through the central hole of the separator disk and into the water reservoir. Prior to filling the reservoir with water, however, the wick was enclosed in a frangible glass shell that extended beyond the end of the wicking reservoir. The end of the shell protruding beyond the water reservoir was surrounded by a flexible plastic sleeve. The purpose of the shell was to keep the wick dry prior to using the device, while the sleeve was included to contain the water when the shell was later compromised. The water reservoir was filled with distilled water.

To begin infusion, the plastic sleeve surrounding the shell was compressed radially between two fingers, shattering it along its length, exposing the wick to the reservoir of distilled water. Once exposed, the wick transported water to the tablet, starting the desorption of carbon dioxide gas and thus beginning the infusion process.

The remainder of the infusion device was similar to that described in Example 6. An administration set, calibrated at 100-mL/h for a 5% dextrose solution, with viscosity expected to be 10–15% greater than the test solution, was clamped shut for the first five minutes following the crushing of the glass shroud. The pressure and volumetric flow rates were monitored over time using a pressure gauge and graduated cylinder and the results are listed in Table 7.

TABLE 7

Infusion Pressure and Liquid Delivery Rate

| Time (min) | Infusion Pressure (PSIG) | Cumulative Delivered Liquid Volume (mL) |
| --- | --- | --- |
| 0 | 2 | Set Clamped Shut |
| 1 | 3.1 | Set Clamped Shut |
| 2 | 6.8 | Set Clamped Shut |
| 3 | 8.5 | Set Clamped Shut |
| 4 | 9.8 | Set Clamped Shut |
| 5 | 10.2 | 0 |
| 10 | 10.3 | 11 |
| 30 | 10.3 | 42 |
| 45 | 10.2 | 65 |
| 70 | 10.2 | 120 |
| 90 | 10.2 | 170 |
| 110 | 10 | 188 |
| 120 | 10 | 207 |
| 140 | 10 | 242 |
| 160 | 9.9 | 268 |

The above data clearly demonstrates that an infusion device can be started via the breakage of a crushable glass-enclosed ampule.

EXAMPLE 10

Use of a Retractable Shell

The basic steps of Example 9 were repeated, except the crushable glass shell shrouded in flexible plastic was replaced with a rigid retractable plastic shell with a pull string at one end, as shown in FIG. 1. To expose the wick to water, the pull string is pulled outward until the shell abuts a stop in the water reservoir. Once the shell is retracted in this manner, the wick is exposed and infusion begins.

The pressure and volumetric flow rates were monitored over time using a standard lab pressure gauge and graduated cylinder and were recorded in Table 8. In generating this data, the device was clamped shut for the first five minutes after wick exposure was initiated to allow the pressure to build to 10 PSIG.

TABLE 8

Infusion Pressure and Liquid Delivery Rate

| Time (min) | Infusion Pressure (PSIG) | Cumulative Delivered Liquid Volume (mL) |
|---|---|---|
| 0 | 3 | — |
| 1 | 7 | — |
| 2 | 9.8 | — |
| 3 | 10 | — |
| 4 | 10.5 | — |
| 5 | 10.5 | 0 |
| 15 | 10.7 | 21 |
| 30 | 10 | 50 |
| 45 | 10 | 76 |
| 60 | 10 | 104 |
| 75 | 10 | 133 |
| 90 | 10 | 160 |
| 120 | 10 | 215 |
| 150 | 10 | 262 |
| 160 | 9.8 | 274 |

The above data demonstrates that an infusion device can be started by retraction of a protective shell.

EXAMPLE 11

Further Use of Infusion Device With $CO_2$-Loaded Zeolite

This example is as further illustration of the use of an infusion device powered with carbon dioxide desorbed from a composite zeolite tablet.

A tablet was formed from 16.5 g of a mixture of 55% by weight zeolite type 4A and 45% by weight zeolite type 13X molecular sieve, mixed with magnesium stearate (0.17 g) and polyester fibers (0.34 g) 0.040–0.060 inch in length by 0.0025 inch in diameter (Type 9001 natural, Cellusuede Products Inc.), using the procedures of Examples 1 and 2.

A flexible device comprising a 100-mL pillow-shaped medication pouch constructed of flexible polyvinyl chloride film was sealingly contained within a flexible, yet nonextensible, oriented 0.001-inch thick polyester film adhesively laminated to flexible polyvinyl chloride LAY-FLAT tube of about 0.008 inch in thickness. The diameter of the tube was about 1.7 inches. This laminated tube was in fluid communication with a source of gas as described in Example 9. When carbon dioxide gas desorbed from the tablet, the gas entered the tube and pressured the inside of the gas-containing tube to about 10 PSIG. Excess gas pressure was relieved via an elastomeric pressure relief valve as shown in FIGS. 4 and 5 set to about 10 PSIG. This pressurized gas exerted pneumatic pressure on all sides of the medication pouch, forcing medication through an attached 50 mL/h infusion set. The infusion set was clamped for the first 5 minutes of gas generation to allow enough gas pressure to build prior to the start of infusion.

The pressure and volumetric flow rates were monitored over time using a pressure gauge and graduated cylinder and were recorded in Table 9. In generating this data, the device was clamped shut for the first five minutes after wick exposure was initiated to allow the pressure to build to 10 PSIG.

TABLE 9

Infusion Pressure and Liquid Delivery Rate

| Time (min) | Infusion Pressure (PSIG) | Cumulative Delivered Liquid Volume (mL) |
|---|---|---|
| 0 | 2.2 | — |
| 1 | 5.8 | — |
| 2 | 8.5 | — |
| 3 | 9.8 | — |
| 4 | 10.5 | — |
| 5 | 10.5 | 0 |
| 10 | 10.2 | 6 |
| 15 | 10.2 | 11 |
| 30 | 10.2 | 27 |
| 45 | 10.2 | 41 |
| 60 | 10 | 49 |
| 75 | 10 | 63 |
| 85 | 9.8 | 72 |
| 100 | 10 | 81 |
| 120 | 10 | 92 |
| 130 | 9.7 | 97 |
| 140 | 9.7 | 101 |
| 150 | 9.6 | 104 |
| 160 | 9.7 | 108 |

The above data demonstrates that a flexible pouch within a pouch can readily be employed as an infusion device.

EXAMPLE 12

Variation in Ratio of Types of Molecular Sieve

This example illustrates the use of composite zeolite tablets with varying proportions of zeolite molecular sieve types 4A and 13X to ran an infusion device and varying flow characteristics.

A 17-g molecular sieve mixture containing 50% by weight 4A zeolite molecular sieve and 50% by weight 13X zeolite molecular sieve was mixed with magnesium stearate (0.175 g) and polyester fibers (0.35 g) 0.040–0.060 inch in length by 0.0025 inch in diameter (Type 9001 natural, Cellusuede Products Inc.), and formed into a carbon dioxide loaded tablet using the general procedures of Examples 1 and 2.

An infusion device as described in Example 6 was used. The infusion device contained 100 mL of liquid to be delivered, with an administration set calibrated at 50 mL/hr for a 5% dextrose solution, viscosity expected to be 10–15% greater than the test solution.

The pressure and volumetric flow rates were monitored over time using a standard lab pressure gauge and graduated cylinder and were recorded in Table 10.

TABLE 10

Infusion Pressure and Liquid Delivery Rate

| Time (min) | Infusion Pressure (PSIG) | Cumulative Delivered Liquid Volume (mL) |
|---|---|---|
| 1 | 4.2 | <10 |
| 2 | 8.2 | <10 |
| 3 | 10.5 | <10 |
| 4 | 10.7 | <10 |
| 5 | 10.9 | <10 |
| 10 | 10.9 | 10 |
| 30 | 10.9 | 27 |
| 40 | 10.9 | 36 |
| 70 | 10.8 | 60 |
| 90 | 10.5 | 76 |
| 110 | 10.4 | 87 |

TABLE 10-continued

Infusion Pressure and Liquid Delivery Rate

| Time (min) | Infusion Pressure (PSIG) | Cumulative Delivered Liquid Volume (mL) |
|---|---|---|
| 120 | 9.8 | 95 |
| 130 | 7.5 | 103 |
| 140 | 6.6 | 108 |

The above data demonstrates that the gas flow rates of an infusion device can be altered by varying the proportions of molecular sieve types used to construct the tablets.

EXAMPLE 13
A Further Variation on the Molecular Sieve Composition

This example illustrates the use of a second small layer comprising of a high percentage of zeolite molecular sieve type 13X to provide a rapid pressure build up of within an infusion device.

A mixture of 12 g of 60% zeolite molecular sieve type 4A and 40% zeolite molecular sieve type 13X, was mixed with magnesium stearate (0.12 g) and polyester fibers (0.24 g) 0.040–0.060 inch in length by 0.0025 inch in diameter (Type 9001 natural, Cellusuede Products Inc.) and formed into a carbon dioxide-loaded tablet using the general procedures of Examples 1 and 2. In addition to this main tablet, type 13X zeolite molecular sieve (1.8 g) was mixed with of the same type of polyester fibers (0.20 g), and prepared into a tablet using the general procedures of Examples 1 and 2.

The second tablet (consisting primarily of type 13X zeolite molecular sieve) was placed beneath the first tablet, and then inserted with a common wick and placed into an infusion device as described in Example 6. In this case, the 100-mL infusion device was connected to an administration set calibrated at 50 mL/h for a 5% dextrose solution, viscosity expected to be 10–15% greater than the test solution.

The pressure and volumetric flow rates were monitored over time using a pressure gauge and graduated cylinder and are shown in Table 11.

TABLE 11

Infusion Pressure and Liquid Delivery Rate

| Time (min) | Infusion Pressure (PSIG) | Cumulative Delivered Liquid Volume (mL) |
|---|---|---|
| 1 | 3.5 | <10 |
| 2 | 5.5 | <10 |
| 3 | 7 | <10 |
| 4 | 8.4 | <10 |
| 5 | 9.5 | <10 |
| 10 | 9.5 | 8 |
| 15 | 9.5 | 13 |
| 20 | 9.5 | 17 |
| 25 | 9.5 | 21 |
| 30 | 9.5 | 26 |
| 35 | 9.3 | 30 |
| 40 | 9.3 | 34 |
| 45 | 9.3 | 38 |
| 50 | 9.3 | 42 |
| 55 | 9.3 | 46 |
| 60 | 9.3 | 50 |
| 65 | 9.3 | 54 |
| 70 | 9.3 | 59 |
| 75 | 9.3 | 63 |
| 80 | 9.3 | 67 |
| 85 | 9.3 | 71 |
| 90 | 9.3 | 74.5 |

TABLE 11-continued

Infusion Pressure and Liquid Delivery Rate

| Time (min) | Infusion Pressure (PSIG) | Cumulative Delivered Liquid Volume (mL) |
|---|---|---|
| 100 | 9.3 | 82 |
| 110 | 9.3 | 90 |
| 120 | 9.5 | 98 |
| 130 | 9.5 | 105 |
| 140 | 9.5 | 114 |
| 150 | 9.5 | 124 |

The above data demonstrates that this type of combination tablet can expedite the rate of initial pressurization of an infusion device.

EXAMPLE 14
Use of Crosslinked Acetalized PVA to Transport Water to Sodium Carbonate/Citric Acid Tablet This example illustrates the use a crosslinked acetalized polyvinyl alcohol wick (Kanebo type E-2) to provide water necessary to mediate the reaction between sodium bicarbonate and citric acid. The reaction is mediated by providing a controlled rate of water delivery to control the quantity and concentration of reactants in solution at any given time.

Sodium bicarbonate (14.7 g) was mixed with citric acid (9.8 g), and anhydrous calcium phosphate (0.25 g, EMCOMPRESS® from Mendell Co.). This mix was formed into a tablet using the general procedure of Example 1. Through the tablet was placed a 0.078"×0.078"×1.6" acetalized polyvinyl alcohol wick (Kanebo type E-2). The tablet and wick were then sealed off inside a rigid PVC assembly, controlled by an elastomeric pressure relief valve set to approximately 10 PSIG. The wick was then exposed to distilled water, allowing the water to wick into the tablet, as in Example 3. The gas generated from this system was used to power a 250-mL infusion device similar to that described in Example 6, with liquid being infused through a 100 mL/h administration set calibrated for a 5% dextrose solution, viscosity expected to be 10–15% greater than the test solution.

The pressure and volumetric flow rates were monitored over time and are shown in Table 12.

TABLE 12

Infusion Pressure and Liquid Delivery Rate

| Time (min) | Infusion Pressure (PSIG) | Cumulative Delivered Liquid Volume (mL) |
|---|---|---|
| 1 | 3.5 | <5 |
| 2 | 11 | <5 |
| 3 | 10.8 | 5 |
| 4 | 10.8 | 7 |
| 5 | 10.2 | 8 |
| 10 | 10 | 18 |
| 20 | 9.5 | 35 |
| 30 | 9.5 | 50 |
| 40 | 9.5 | 66 |
| 70 | 9.9 | 120 |
| 90 | 10 | 156 |
| 110 | 9 | 194 |
| 140 | 8.4 | 231 |
| 160 | 8.4 | 270 |
| 180 | 9.6 | all liquid delivered |

EXAMPLE 15

Use of a Solid Phase Enzyme

This example illustrates the use of hydrogen peroxide solution and a tablet containing an enzyme capable of decomposing hydrogen peroxide to run an infusion device.

Thirty-six OXYSEPT® 2 neutralizing enzyme tablets (Allergan Inc., Irvine, Calif., USA) (3.2 g) were crushed into a fine powder and mixed with polyvinyl pyrrolidone (1 g, ISP Technologies K-25). This mixture was then formed into a tablet using the general procedures of Example 1.

An aqueous solution of 8% hydrogen peroxide was then drawn into the tablet through an acetalized polyvinyl alcohol (Kanebo type E-2) wick as described in Example 3. The resulting oxygen which was generated from the enzymatic decomposition of hydrogen peroxide was used to power a 250-mL device as described in Example 6, with liquid being delivered through an administration set calibrated at 100 mL/h for a 5% dextrose solution, viscosity expected to be 10–15% greater than the test solution.

The pressure and volumetric flow rates were monitored for 10 minutes, until the peroxide was completely exhausted. The data was recorded in Table 13.

TABLE 13

Infusion Pressure and Liquid Delivery Rate

| Time (min) | Infusion Pressure (PSIG) | Cumulative Delivered Liquid Volume (mL) |
| --- | --- | --- |
| 1 | 6 | 1 |
| 2 | 11.2 | 3 |
| 3 | 10.8 | 5 |
| 4 | 10.6 | 7 |
| 5 | 10.6 | 9 |
| 6 | 10.4 | 12 |
| 7 | 10.2 | 14 |
| 8 | 10.2 | 16 |
| 9 | 10 | 18 |
| 10 | 9.5 | 20 |

EXAMPLE 16

Driving Infusion Device without Use of a Discrete Wick

This example illustrates the desorption of gas from a sorbent material to power an infusion device without the use of a discrete wick. In this example, zeolite molecular sieve type 13X (5.4 g) was mixed with magnesium stearate (0.53 g) and prepared into a 1-inch diameter, solid cylindrical tablet using the compaction method described in Example 1. Unlike the tablets in preceding examples, this tablet contained no center hole. Once formed, the tablet was activated and loaded with carbon dioxide using the methods of Example 2.

A 35-g solution containing 70% by weight polyethylene glycol 600 (J. T. Baker, Phillipsburg, N.J., USA) and 30% by weight distilled water was prepared and placed inside a small pressure vessel. To begin the desorption process, the sorbent tablet was then dropped onto the solution. Upon contact with the solution the sorbent tablet desorbed carbon dioxide gas in a controlled manner.

The volume of carbon dioxide gas desorbed from the tablet was recorded and is listed in Table 14.

TABLE 14

Gas Desorption Rate

| Time (min) | Cumulative Desorbed $CO_2$ Volume (mL) |
| --- | --- |
| .5 | 40 |
| 1 | 48 |
| 2 | 58 |
| 3 | 66 |
| 4 | 73 |
| 5 | 80 |
| 6 | 87 |
| 7 | 92 |
| 8 | 97 |
| 9 | 103 |
| 10 | 107 |
| 11 | 114 |

While this experiment did not include the use of an infusion device, the data demonstrates that an infusion device can be run using only a loaded molecular sieve sorbent tablet and an aqueous solution to affect a controlled desorbing of gas without the use of a discrete wick.

EXAMPLE 17

Use of a Hydrogel

This example illustrates the desorption of gas from a sorbent material to power an infusion device using a bed of hydrogel.

Zeolite molecular sieve type 13X (2 g) was mixed with magnesium stearate (0.5 g) and formed into a 0.5-inch diameter, solid cylindrical tablet using the compaction method of tableting similar to that described in Example 1. No center hole was formed in the tablet. The sorbent tablet was activated and loaded with carbon dioxide using the general procedures of Example 2.

A sheet of hydrogel (2"×2"× about 1/16" thick, 2ND SKIN® Non-stick Moist Burn Pads, Spenco Medical Corporation, Haywards Heath, United Kingdom) was placed on the bottom surface of a small pressure vessel. To begin gas desorbing, the loaded sorbent tablet was placed on top of the hydrogel sheet. This placement allowed the tablet to adsorb water at a slow rate from the hydrogel, and in turn desorb the adsorbed gas.

The volume of carbon dioxide desorbed from the tablet over time is shown in Table 15.

TABLE 15

Gas Desorption Rate

| Time (min) | Cumulative Desorbed $CO_2$ Volume (mL) |
| --- | --- |
| 0 | 54 |
| 1 | 72 |
| 2 | 80 |
| 3 | 88 |
| 4 | 92 |
| 5 | 96 |
| 6 | 99 |
| 7 | 102 |
| 8 | 104 |
| 9 | 107 |
| 10 | 108 |
| 11 | 110 |

TABLE 15-continued

Gas Desorption Rate

| Time (min) | Cumulative Desorbed $CO_2$ Volume (mL) |
|---|---|
| 12 | 112 |
| 13 | 113 |
| 14 | 114 |
| 15 | 116 |
| 16 | 118 |
| 17 | 118 |
| 18 | 120 |
| 19 | 121 |
| 20 | 122 |
| 25 | 127 |
| 30 | 132 |
| 35 | 137 |

The above data demonstrates that an infusion device can be run using only a sorbent tablet and a hydrogel bed upon which it is placed. It also shows that liquid water or water containing solution is not absolutely necessary for desorption of gas from a sorbent loaded tablet.

The foregoing is offered primarily for purposes of illustration. It will be readily apparent to those skilled in the art that the component shapes and dimensions, materials, operating conditions, procedural steps and other parameters of the inventions described herein may be further modified or substituted in various ways without departing from the spirit and scope of the inventions.

We claim:

1. An article of manufacture comprising:

a solid substance;

a liquid-retaining receptacle for retaining a liquid substance which upon contact with said solid substance generates a gaseous product, said liquid-retaining receptacle permitting contact of said liquid substance with said solid substance through diffusive transport of said liquid substance, said solid substance being external of said liquid-retaining receptacle and separated from the interior thereof by a receptacle wall having a passage therethrough; and a wick in contact with said solid substance and extending through said passage into said interior of said receptacle for limiting diffusion of said liquid substance toward said solid substance to a controlled rate to achieve diffusion-controlled generation of said gaseous product, said wick comprised of a member selected from the group consisting of crosslinked polyvinyl alcohol and combinations of crosslinked polyvinyl alcohol and crosslinked polyvinyl acetate.

2. An article of manufacture comprising:

a molecular sieve impregnated with carbon dioxide;

pores in said molecular sieve for retaining a liquid substance which upon contact with said molecular sieve generates a gaseous product, said pores permitting contact of said liquid substance with said molecular sieve through diffusive transport of said liquid substance;

a liquid diluent combined with said liquid substance to form a solution for limiting diffusion of said liquid substance toward said solid substance to a controlled rate to achieve difflusion-controlled generation of said carbon dioxide.

3. An article of manufacture in accordance with claim, 2 in which said liquid diluent is a polyalkylene glycol.

4. An article of manufacture in accordance with claim 2 in which said liquid diluent is a polyethylene glycol with a weight averaged molecular weight of from about 400 to about 600.

5. An article of manufacture in accordance with claim 4 in which said polyethylene glycol constitutes from about 1% to about 90% by weight of said solution.

6. An article of manufacture in accordance with claim 4 in which said polyethylene glycol constitutes from about 20% to about 60% by weight of said solution.

7. An article of manufacture comprising:

a molecular sieve impregnated with carbon dioxide;

pores in said molecular sieve for retaining a liquid substance which upon contact with said molecular sieve generates a gaseous product, said pores permitting contact of said liquid substance with said molecular sieve through diffusive transport of said liquid substance; and a solute dissolved in said liquid substance to form a solution having a viscosity greater than that of said liquid substance alone.

8. An article of manufacture in accordance with claim 7 in which said solute is a member selected from the group consisting of cellulose and cellulose derivatives.

9. An article of manufacture in accordance with claim 7 in which said solute is hydroxy ethyl cellulose.

10. An article of manufacture in accordance with claim 9 in which said hydroxy ethyl cellulose constitutes from about 0.1% to about 5% by weight of said solution.

11. Apparatus for dispensing a liquid at a controlled rate, said apparatus comprising:

a bladder to contain said liquid, said bladder containing an opening;

a housing of substantially gas-impermeable wall material defining a cavity to receive said bladder while leaving said opening exposed;

a solid substance and a liquid substance which upon contact with each other generate a gaseous product, said solid and liquid substances further received within said housing and external to said bladder, said liquid substance being retained within a liquid-retaining receptacle and said solid substance being external of said receptacle;

a wick communicating said solid substance with the interior of said liquid receptacle and contacting said solid and liquid substances by diffusive transport of said liquid substance toward said solid substance at a controlled rate to achieve diffusion-controlled generation of said gaseous product, said wick comprised of a member selected from the group consisting of crosslinked polyvinyl alcohol and combinations of crosslinked polyvinyl alcohol and crosslinked polyvinyl acetate.

12. Apparatus in accordance with claim 11 in which said solid substance and said liquid substance are separated by a wall of said receptacle, said wall having a passage therethrough, and said wick extending through said passage.

13. Apparatus in accordance with claim 11 further comprising a pressure relief valve in said housing external to said bladder.

14. Apparatus in accordance with claim 13 in which said pressure relief valve is comprised of an elastomeric sleeve surrounding a stem in sealing relationship, yet separable from said stem upon the exertion of a threshold gas pressure therebetween, thereby releasing pressure from said housing when said threshold pressure is exceeded.

15. Apparatus in accordance with claim 14 in which said stem has an outer surface with a taper, and the location of said elastomeric sleeve relative to said taper is variable to thereby vary said threshold gas pressure.

16. Apparatus in accordance with claim 14 in which said elastomeric sleeve is constructed of poly(methyl vinyl siloxane).

17. Apparatus in accordance with claim 14 further comprising a lubricant between said elastomeric sleeve and said stem.

18. Apparatus in accordance with claim 11 in which said housing comprises an inner lamina of polyvinyl chloride and an outer lamina of oriented polyester, and is sufficiently flexible to permit said apparatus to be collapsed and folded to reduce its volume for purposes of storage.

19. Apparatus in accordance with claim 18 in which said inner lamina is from about 0.01 cm to about 0.05 cm in thickness, and said outer lamina is from about 0.001 cm to about 0.005 cm in thickness.

20. Apparatus for dispensing a liquid at a controlled rate, said apparatus comprising:
 a bladder to contain said liquid, said bladder containing an opening;
 a housing of substantially gas-impermeable wall material defining a cavity to receive said bladder while leaving said opening exposed;
 a molecular sieve impregnated with carbon dioxide, and water, said molecular sieve and water further received within said housing and external to said bladder; and
 a liquid diluent combined with said water to form a solution, said liquid diluent causing diffusive transport of said water toward said molecular sieve at a controlled rate to achieve diffusion-controlled generation of said carbon dioxide.

21. Apparatus in accordance with claim 20 in which said liquid diluent is polyethylene glycol with a weight averaged molecular weight of from about 400 to about 600.

22. Apparatus for dispensing liquid at a controlled rate, said apparatus comprising:
 a bladder to contain said liquid, said bladder containing an opening;
 a housing of substantially gas-impermeable wall material defining a cavity to receive said bladder while leaving said opening exposed;
 a molecular sieve impregnated with carbon dioxide and water; and
 a solute dissolved in said water to form a solution having a viscosity greater than that of said water alone.

23. Apparatus in accordance with claim 22 in which said solute is a member selected from the group consisting of cellulose and cellulose derivatives.

24. Apparatus in accordance with claim 22 in which said solute is hydroxy ethyl cellulose at a concentration of from about 0.1% to about 5% by weight of said solution.

25. Apparatus for dispensing a liquid at a controlled rate, said apparatus comprising:
 a bladder to contain said liquid, said bladder containing an opening;
 a housing of substantially gas-impermeable wall material defining a cavity to receive said bladder while leaving said opening exposed;
 an aqueous liquid and a molecular sieve material with a gas adsorbed thereto, said aqueous liquid and said molecular sieve material both enclosed within said housing and positioned external to said bladder, whereby gas released from adsorption by said molecular sieve material upon contact of said aqueous liquid with said molecular sieve material causes compression of said bladder and consequently expulsion of liquid from said bladder through said opening.

26. Apparatus for dispensing a liquid at a controlled rate, said apparatus comprising:
 a bladder to contain said liquid, said bladder containing an opening;
 a housing of substantially gas-impermeable wall material defining a cavity to receive said bladder while leaving said opening exposed;
 a liquid solution of a member selected from the group consisting of hydrogen peroxide and superoxide compounds, and a liquid absorbent material having immobilized thereon a member selected from the group consisting of catalysts and enzymes active in releasing oxygen gas from hydrogen peroxide and superoxide compounds, said liquid solution and said liquid absorbent material both enclosed within said housing and positioned external to said bladder, whereby gaseous oxygen released from said liquid solution causes compression of said bladder and consequently expulsion of liquid from said bladder through said opening.

27. Apparatus in accordance with claim 26 in which said liquid solution is an aqueous solution.

28. Apparatus in accordance with claim 26 in which said liquid absorbent material has an enzyme immobilized thereon.

29. Apparatus in accordance with claim 26 in which said liquid absorbent material has a lyophilized catalase immobilized thereon.

30. Apparatus in accordance with claim 26 in which said liquid absorbent material has a catalyst deposited thereon.

31. Apparatus in accordance with claim 26 in which said liquid absorbent material is a member selected from the group consisting of reconstituted cellulose products, superabsorbent polymers, and molecular sieves, and has a member selected from the group consisting of platinum, palladium, and silver deposited thereon.

32. Apparatus in accordance with claim 26 in which said liquid solution is an aqueous solution of hydrogen peroxide.

* * * * *